(12) United States Patent
Peliks

(10) Patent No.: US 11,064,981 B2
(45) Date of Patent: Jul. 20, 2021

(54) TISSUE REMOVAL DEVICE AND METHOD OF USE

(71) Applicant: MERIT MEDICAL SYSTEMS, INC., South Jordan, UT (US)

(72) Inventor: Robert Bilgor Peliks, San Francisco, CA (US)

(73) Assignee: Merit Medical Systems, Inc., South Jordan, UT (US)

(*) Notice: Subject to any disclaimer, the term of this patent is extended or adjusted under 35 U.S.C. 154(b) by 502 days.

(21) Appl. No.: 15/673,076

(22) Filed: Aug. 9, 2017

(65) Prior Publication Data

US 2017/0333011 A1 Nov. 23, 2017

Related U.S. Application Data

(63) Continuation of application No. 14/930,928, filed on Nov. 3, 2015, now Pat. No. 9,763,648, which is a continuation of application No. 14/517,873, filed on Oct. 19, 2014, now Pat. No. 9,204,867, which is a continuation-in-part of application No. PCT/US2014/052431, filed on Aug. 24, 2014.

(60) Provisional application No. 61/872,674, filed on Aug. 31, 2013, provisional application No. 61/872,678, filed on Aug. 31, 2013.

(51) Int. Cl.
*A61B 10/02* (2006.01)
*A61B 10/04* (2006.01)
*A61B 17/32* (2006.01)

(52) U.S. Cl.
CPC ...... *A61B 10/0266* (2013.01); *A61B 10/0275* (2013.01); *A61B 10/04* (2013.01); *A61B 17/320016* (2013.01); *A61B 2010/0208* (2013.01); *A61B 2017/32004* (2013.01)

(58) Field of Classification Search
CPC . A61B 10/0266; A61B 10/0275; A61B 10/04; A61B 17/320016
USPC .......................................................... 600/567
See application file for complete search history.

(56) References Cited

U.S. PATENT DOCUMENTS

| | | |
|---|---|---|
| 3,605,721 A | 9/1971 | Hallac |
| 4,310,969 A | 1/1982 | Cannizzaro et al. |
| 4,651,752 A | 3/1987 | Fuerst |
| 4,781,202 A | 11/1988 | Janese |
| 4,785,826 A | 11/1988 | Ward |
| 5,224,488 A | 7/1993 | Neuffer |
| 5,462,062 A | 10/1995 | Rubinstein et al. |

(Continued)

FOREIGN PATENT DOCUMENTS

| | | |
|---|---|---|
| JP | 2000116657 | 4/2000 |
| WO | WO 2012/068315 A1 | 5/2012 |

(Continued)

OTHER PUBLICATIONS

Euproean Search Report of related foreign application No. 14841120.0 dated Jul. 11, 2017.

(Continued)

*Primary Examiner* — Daniel L Cerioni
(74) *Attorney, Agent, or Firm* — Stoel Rives LLP

(57) ABSTRACT

A biopsy device for acquiring a tissue sample is disclosed. The biopsy device comprises a partoff mechanism which can have at least a tab and an actuator. The actuator can be used to control the angle of the tab and thus partoff a tissue sample. The tab may be on a cutter tube, which may have a sharp distal end which may core the samples from the mass of tissue. Multiple tissue samples may be collected.

13 Claims, 6 Drawing Sheets

(56) References Cited

U.S. PATENT DOCUMENTS

| | | |
|---|---|---|
| 5,823,971 A | 10/1998 | Robinson et al. |
| 5,910,121 A | 6/1999 | Paolo et al. |
| 6,110,128 A | 8/2000 | Andelin et al. |
| 6,330,750 B1 | 12/2001 | Meckel |
| 6,387,056 B1 | 5/2002 | Kieturakis |
| 6,416,484 B1 | 7/2002 | Miller et al. |
| 6,551,254 B2 | 4/2003 | Nishtalas et al. |
| 7,635,340 B2 | 12/2009 | Vetter et al. |
| 7,722,550 B2 | 5/2010 | McClellan |
| 7,758,514 B2 | 7/2010 | Grigoryants et al. |
| 8,317,727 B2 | 11/2012 | Peliks |
| 8,337,414 B2 | 12/2012 | Vetter et al. |
| 8,444,573 B2 | 5/2013 | Flatland et al. |
| 8,475,393 B1 | 7/2013 | Hameed et al. |
| 9,155,527 B2 | 10/2015 | Vetter et al. |
| 9,230,535 B2 | 1/2016 | Yano |
| 9,271,700 B2 | 3/2016 | Peliks |
| 9,320,535 B2 | 4/2016 | Zaretzka |
| 2003/0125639 A1 | 7/2003 | Fisher et al. |
| 2004/0176789 A1 | 9/2004 | Lee et al. |
| 2006/0184198 A1 | 8/2006 | Bales et al. |
| 2006/0224082 A1 | 10/2006 | Vetter et al. |
| 2007/0027464 A1 | 2/2007 | Way et al. |
| 2009/0227893 A1 | 9/2009 | Coonahan et al. |
| 2010/0160827 A1 | 6/2010 | Buressiniani |
| 2010/0222700 A1 | 9/2010 | Hibner |
| 2011/0004120 A1 | 1/2011 | Drubetsky |
| 2012/0172752 A1 | 7/2012 | Ranpura et al. |
| 2012/0209141 A1 | 8/2012 | Peliks |
| 2012/0265217 A1 | 10/2012 | Drews et al. |
| 2013/0172895 A1 | 7/2013 | Wallace et al. |
| 2014/0039343 A1 | 2/2014 | Mescher et al. |
| 2014/0128769 A1 | 5/2014 | Vetter |
| 2014/0277045 A1 | 9/2014 | Fazio et al. |

FOREIGN PATENT DOCUMENTS

| | | |
|---|---|---|
| WO | 2012075409 | 6/2012 |
| WO | WO 2012/075409 A1 | 6/2012 |
| WO | 2012167216 | 12/2012 |
| WO | WO 2012/167216 A2 | 12/2012 |

OTHER PUBLICATIONS

International Search Report of related Foreign Application PCT/US2014/052431 dated Dec. 18, 2014.
Written Opinion of related Foreign Application PCT/US2014/052431 dated Dec. 18, 2014.
International Search Report and Written Opinion dated Dec. 18, 2014 for PCT/US2014/052431.
European Search Report dated Jan. 22, 2019 for EP14841120.0.

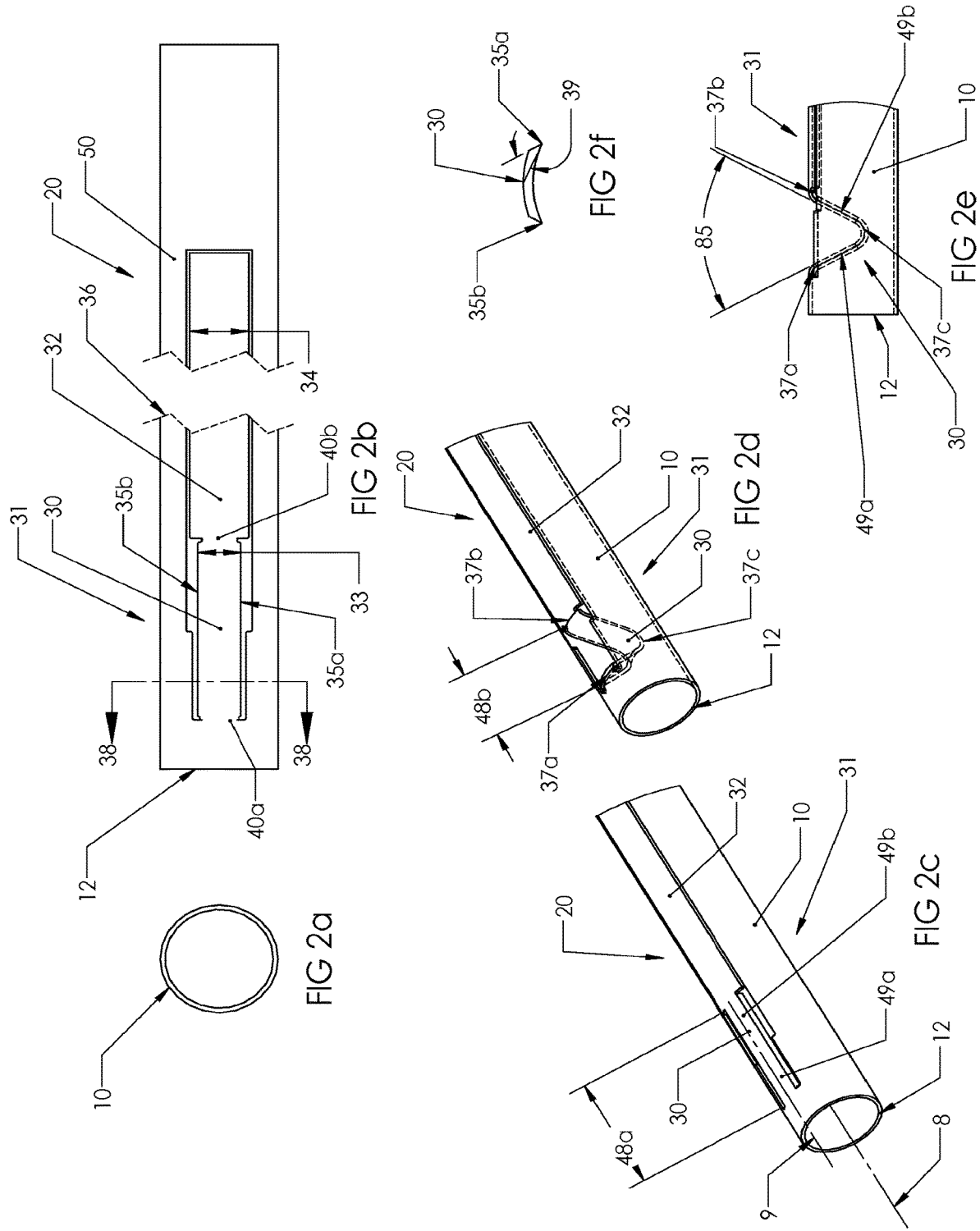

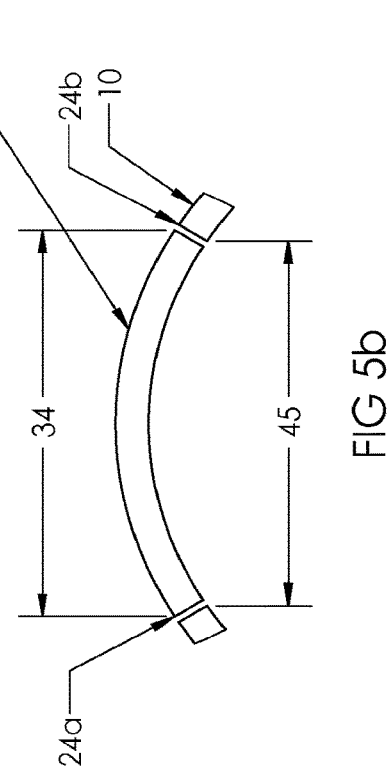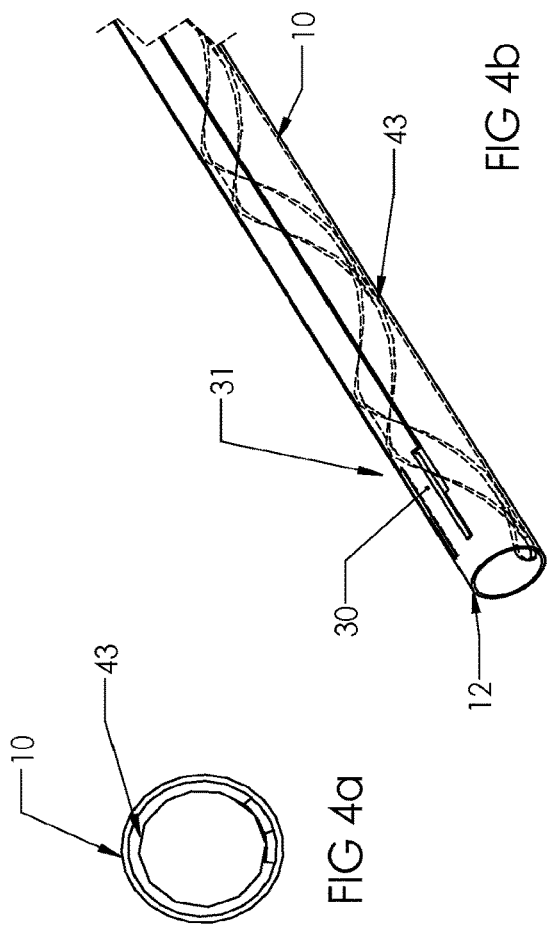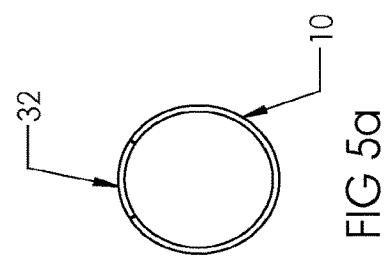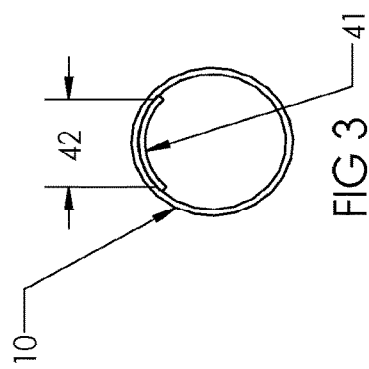

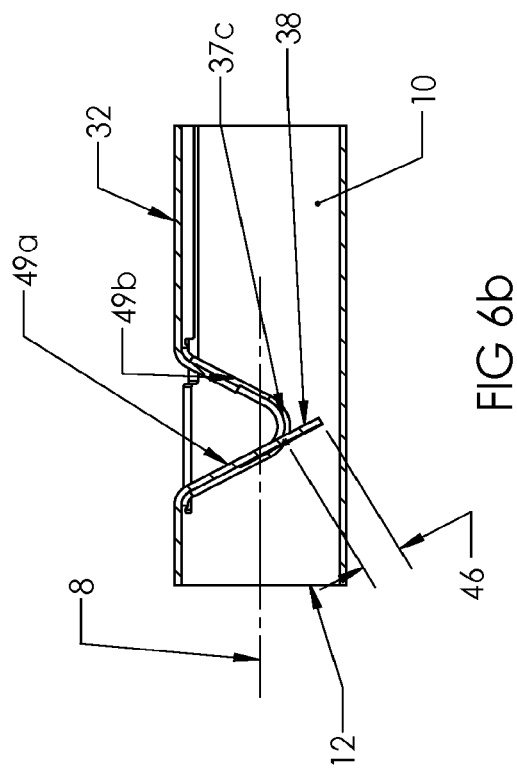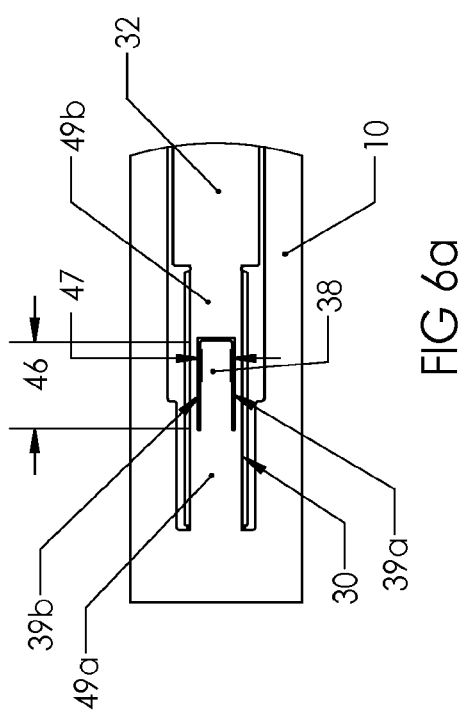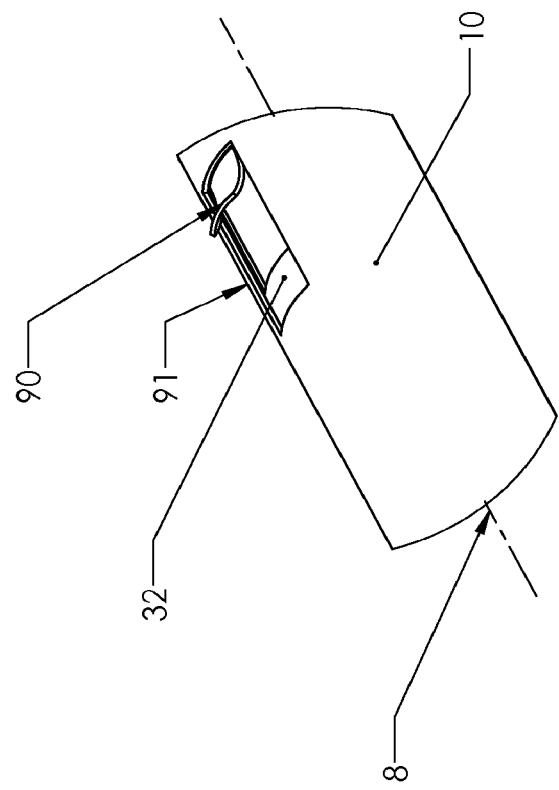

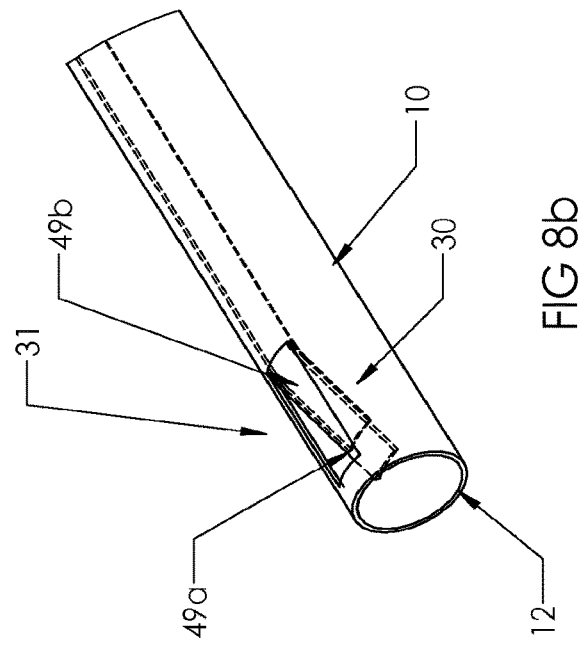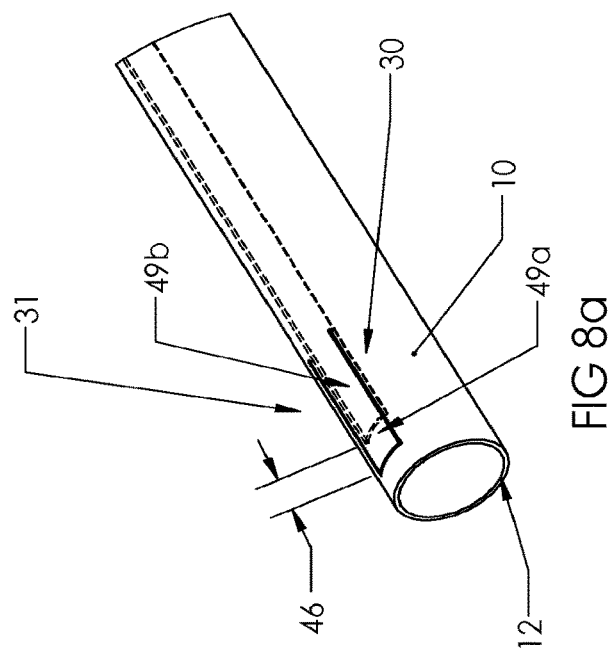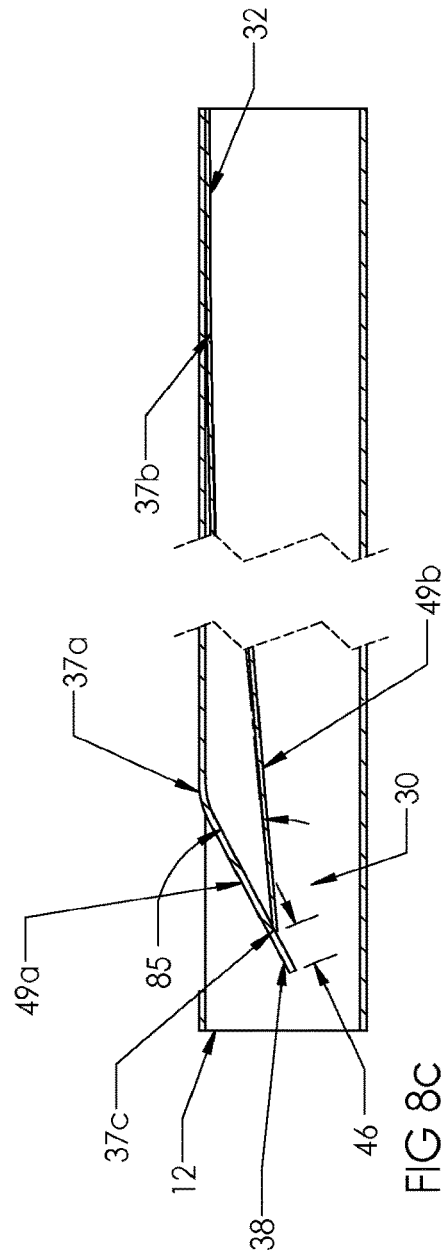

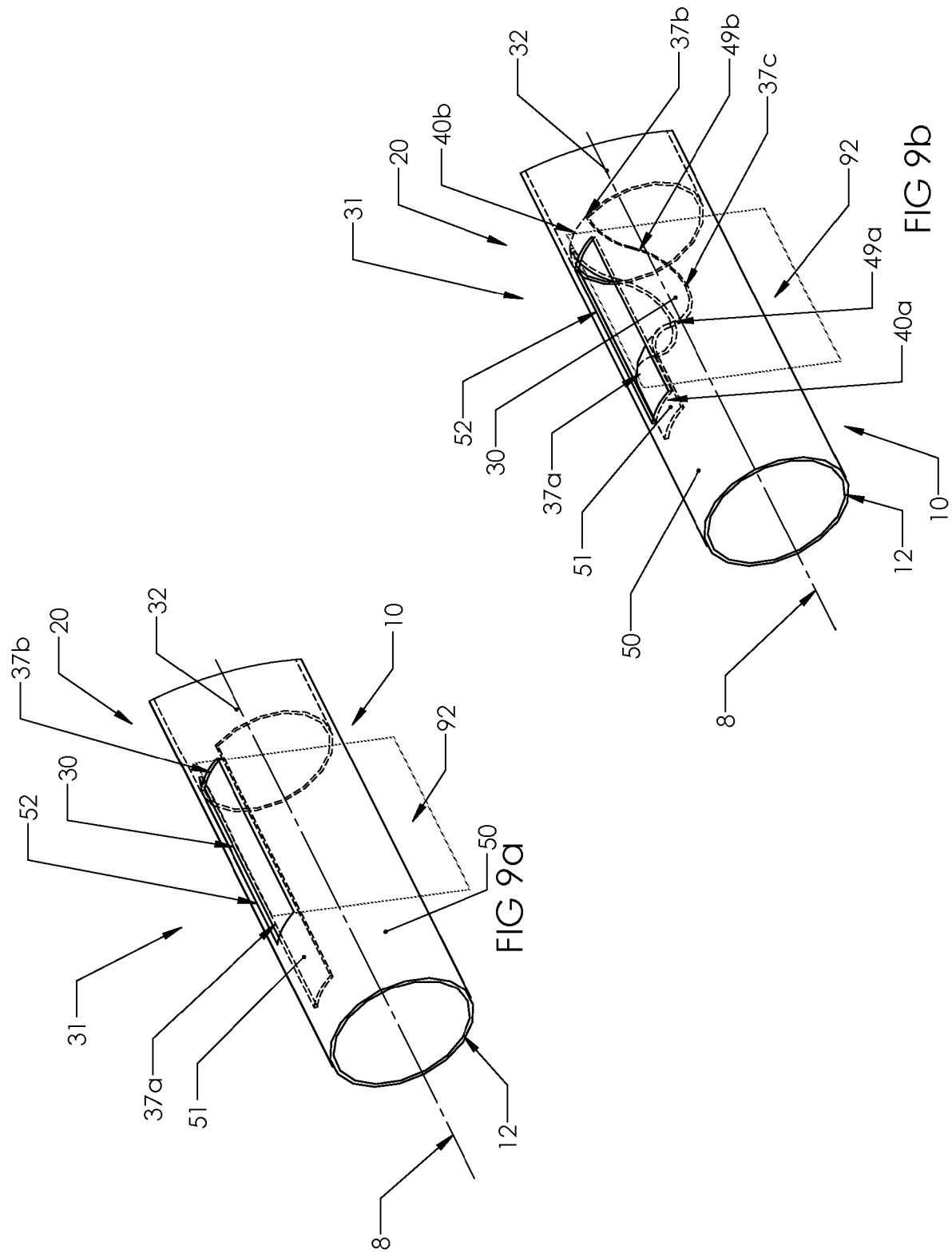

TISSUE REMOVAL DEVICE AND METHOD OF USE

CROSS-REFERENCE TO RELATED APPLICATIONS

This application is a continuation of U.S. application Ser. No. 14/930,928, filed on Nov. 3, 2015, which is a continuation of U.S. application Ser. No. 14/517,873, filed Oct. 19, 2014, now issued as U.S. Pat. No. 9,204,867, which is a continuation-in-part of PCT International Application No. PCT/US 2014/052,431 filed Aug. 26, 2014, which claims the benefit of U.S. Provisional Application Nos. 61/872,678, filed Aug. 31, 2013, and 61/872,674, filed Aug. 31, 2013, each of which are incorporated by reference herein in their entireties.

BACKGROUND OF THE INVENTION

Field of the Invention

This invention relates to medical instrumentation. More particularly, a tool used for acquiring tissue and a method for using the same are disclosed.

Description of the Prior Art

A number of medical procedures require the removal of tissue samples from a patient. These operations can range from the removal of suspicious tissue, as in the biopsy of a cancerous lesion, to cell harvesting, as in a bone marrow donation. A number of different biopsy tools are used for retrieving these tissue samples from patients. One style of biopsy tool may be called forward coring. A forward coring biopsy tool may include a spinning cannula with a razor edge. As the device is advanced into a tissue mass, the cannula may core the tissue. The cored tissue sample must then be parted off from the remaining tissue mass. There are a number of methods for parting off the tissue sample, such as tearing or cutting. There are two main styles of core biopsy tools—side cutting and forward coring.

SUMMARY OF THE INVENTION

A tool used to obtain tissue samples is disclosed herein. The partoff mechanism of the tool can be comprised of at least one tubular element. The tubular element may be spun along a central axis. The distal end of the tubular element may comprise a flexible partoff tab. The angle of this partoff tab may be adjusted during use. For example, the partoff tab may be flush with the remainder of the tube wall while advancing the device into a mass of tissue & while coring a tissue sample; the partoff tab may be angled inwards to partoff the sample from the tissue mass. The tube may be spinning as the partoff tab is repositioned; if the tube is spinning, the partoff tab may cut the tissue mass as it is being repositioned. The partoff tab may remain positioned inwards to secure the samples within the tubular element (e.g. the partoff tab may prevent the samples from falling out of the terminal distal end of the tubular element).

A tool for acquiring tissue is disclosed. The tool can have a cutter tube comprising a tubular system and a partoff tab. The partoff tab may have a partoff tab first end and a partoff tab second end. The partoff tab first end can be secured to the tubular system. The partoff tab second end can be secured to the tubular system. The cutter tube can have a tubular longitudinal axis. The partoff tab can have a longitudinally expanded configuration and a longitudinally contracted configuration. The length of the partoff tab along the tubular longitudinal axis in the longitudinally expanded configuration may be longer than the length of the partoff tab in the longitudinally contracted configuration.

A tool for acquiring tissue may be comprised of a cutter tube, a partoff tab having a partoff tab first and second ends and an actuator. The partoff tab first end can be secured to the cutter tube. The partoff tab second end can be secured to the actuator. The length of the partoff tab along the tubular longitudinal axis in the longitudinally expanded configuration may be longer than the length of the partoff tab in the longitudinally contracted configuration.

A tool for acquiring tissue may comprise a cutter tube. The cutter tube may comprise the tubular system and the partoff tab. The length of the partoff tab along a tubular longitudinal axis in the longitudinally expanded configuration may be longer than the length of the partoff tab in the longitudinally contracted configuration. The partoff tab can have two flex points, when in the contracted configuration.

A tool for acquiring tissue may comprise a cutter tube. The cutter tube may comprise the tubular system and the partoff tab. The length of the partoff tab along a tubular longitudinal axis in the longitudinally expanded configuration may be longer than the length of the partoff tab in the longitudinally contracted configuration. The partoff tab can has one inflection point, when in the contracted configuration.

A tool for acquiring tissue may comprise a cutter tube, a partoff tube and an actuator. The partoff tab can have two flex points, when in the contracted configuration.

A tool for acquiring tissue may comprise a cutter tube, a partoff tube and an actuator. The partoff tab can has one inflection point, when in the contracted configuration.

A method for operating a mass removal device is disclosed. The mass removal device may comprise a cutter tube, comprising the tubular system and the partoff tab. The partoff tab can have a partoff tab first end and a partoff tab second end. The partoff tab first end can be secured to the tubular system. The partoff tab second end can be secured to the tubular system. The method can comprise actuating the partoff tab, wherein the actuating comprises extending the partoff tab radially inwardly or outwardly relative to the cutter tube.

A method for operating a mass removal device is disclosed. The mass removal device may comprise a cutter tube, an actuator and a partoff tab. The partoff tab can have a partoff tab first end and a partoff tab second end. The partoff tab first end can be secured to the cutter tube. The partoff tab second end can be secured to the actuator. The method can comprise actuating the partoff tab, wherein the actuating comprises extending the partoff tab radially inwardly or outwardly relative to the cutter tube.

BRIEF DESCRIPTION OF THE DRAWINGS

FIG. 2a through FIG. 2f illustrate different views of the cutter tube. FIG. 2a is a distal end view of the cutter tube, FIG. 2b is a broken top view of a portion of the cutter tube (the middle portion has been removed for illustrative purposes), FIG. 2c is an isometric view of the distal end of the cutter tube in the coring configuration, FIG. 2d is an isometric view of the distal end of the cutter tube in the partoff configuration (hidden lines are shown for illustrative purposes), FIG. 2e is a side view of the distal end of the cutter tube in the part off configuration (hidden lines are shown for illustrative purposes) and FIG. 2f is a cross-sectional view of the tab taken at tab section 38.

FIG. 3 is a distal view of the cutter tube with a straight internal reinforcement.

FIG. 4a is a distal view of the cutter tube with a spiral internal reinforcement and FIG. 4b is an isometric view of the distal end of the cutter tube with a spiral reinforcement (hidden are shown for illustrative purposes).

FIG. 5a is a cross-sectional view of the cutter tube with a wedged partoff mechanism taken at actuator section 36 of FIG. 2b; and FIG. 5b is an enlarged detail view of the top portion of FIG. 5a.

FIG. 6a is a top view of the distal end of the cutter tube and partoff mechanism in the coring configuration. FIG. 6b is a cross-sectional side view of the distal end of the cutter tube and partoff mechanism in the partoff configuration.

FIG. 7 is an isometric view illustrating a limiting tab.

FIG. 8a is an isometric view of the distal end of a bimetal partoff tab in the coring configuration, FIG. 8b is an isometric view of the distal end of a bimetal partoff tab in the partoff configuration (hidden lines are shown for illustrative purposes); and FIG. 8c is a broken, cross-sectional side view of the bimetal partoff tab in the partoff configuration.

FIG. 9a illustrates a partoff mechanism in the coring configuration and FIG. 9b illustrates a partoff mechanism in the partoff configuration.

DETAILED DESCRIPTION

Figure 1:
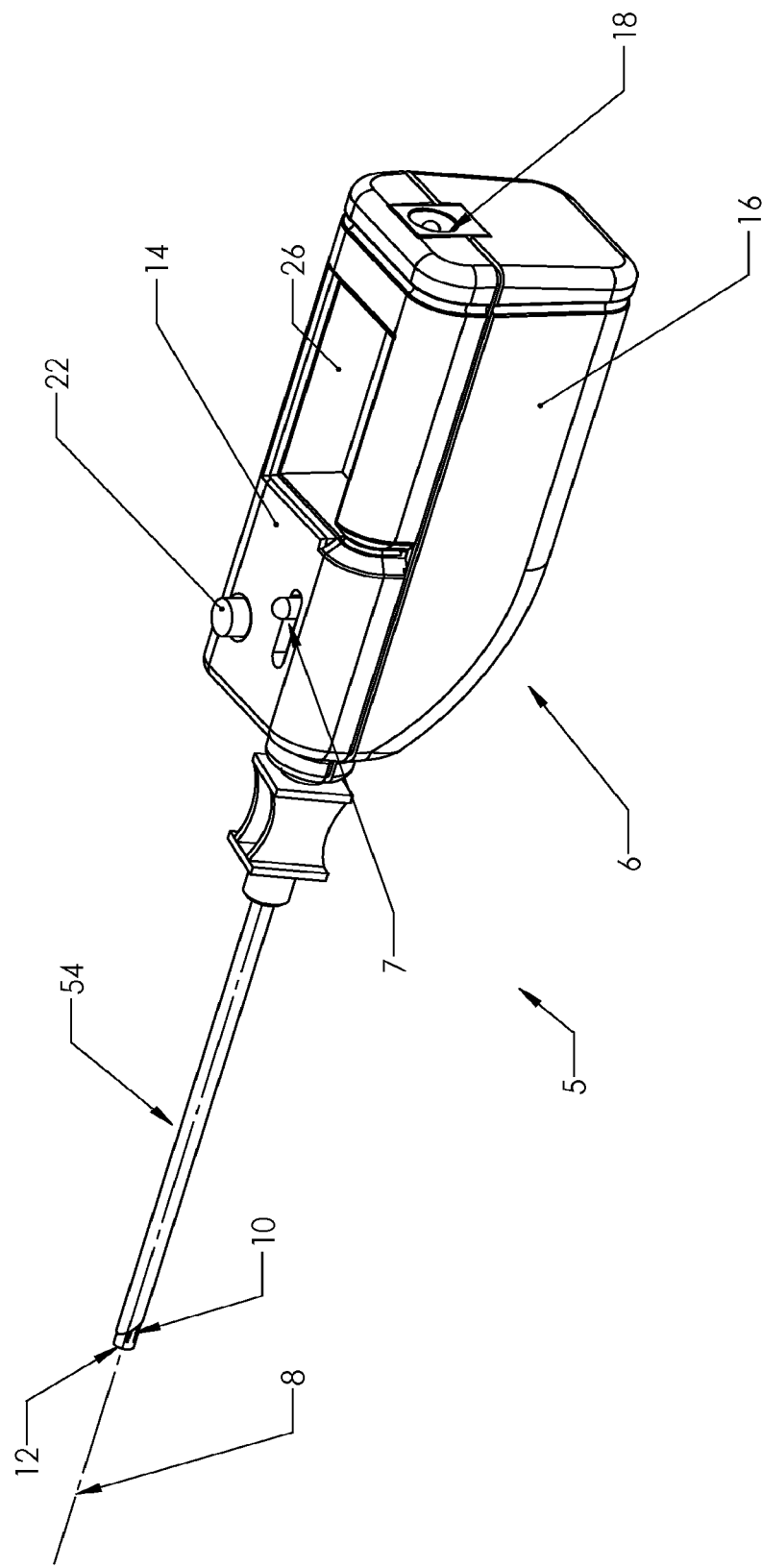
FIG. 1 is an illustrative isometric view of a variation of the tool.

FIG. 1 illustrates a tool 5 that can be sterilized. The tool 5 may have an ergonomic handle 6. The handle 6 can have a handle top portion 14 joined together with a handle bottom portion 16. The tool 5 may have a handle left portion and a handle right portion. The handle top portion 14 and the handle bottom portion 16 may be injection molded. The handle 6 may contain a cutter tube 10. The cutter tube 10 can be rotatable about a tubular longitudinal axis 8 or rotationally-fixed with respect to the handle 6. The cutter tube 10 can extend distally from the handle 6 and can have a cutter tube terminal distal end 12. The handle 6 can have an electrical connection 18 which can connect to an external power supply. The tool 5 could instead, or in combination with an external power supply, be powered with internal batteries, mechanically, hydraulically or pneumatically. A cover may enclose the samples in a collection chamber 26. The cover may be removed or adjusted to provide physical access to the samples stored in the collection chamber 26. The cover can be transparent, translucent, or opaque. The rotation of the cutter tube 10 may be controlled by actuating a coring button 22. A partoff button 7 may actuate a partoff mechanism 31. The partoff button 7 and the coring button 22 may be the same button; for example, a button could have multiple positions and depending on the position may actuate the partoff mechanism 31 and/or rotate the cutter tube 10. A coaxial introducer 54 may be secured to the handle 6. The coaxial introducer 54 may be comprised of a tube and a luer fitting. The luer fitting of the coaxial introducer 54 may secure the coaxial introducer 54 to the handle 6. The tube of the coaxial introducer 54 may have a clearance fit with the cutter tube 10. For example, the gap between the cutter tube 10 and the coaxial introducer 54 may be between 0.001 to 0.006in (0.02 to 0.15mm).

FIG. 2a illustrates that the cutter tube 10 may have a round cross-section. The cutter tube 10 may be manufactured from stainless steel hypodermic tubing (i.e., hypotube). For example, the cutter tube 10 may be manufactured from full hard 304SS hypotube. The hypotube may be welded and drawn. The hypotube may be ground (e.g., centerless ground and/or plugged and ground).

FIG. 2b illustrates that the cutter tube 10 may have the partoff mechanism 31. One example of the partoff mechanism 31 may be comprised of a partoff tab 30 and an actuator 32. The cutter tube 10 may be comprised of the partoff tab 30 and a tubular system 20; the tubular system 20 may be comprised of the actuator 32 and a tubular structure 50. The cutter tube 10 can have a partoff tab 30, the actuator 32, the tubular system 20, the tubular structure 50, or combinations thereof. For example, the partoff tab 30 and the actuator 32 may be formed by laser cutting and/or stamping the cutter tube 10. The partoff tab 30 and the actuator 32 may be a separate piece of material that may be adhered to the cutter tube 10. For example, the cutter tube 10 may have a window cut out and an element comprising the partoff tab 30 and/or the actuator 32 may be secured (e.g., welded and/or glued) to the cutter tube 10. The partoff tab 30 may have a partoff tab width 33. The actuator 32 may have an actuator width 34. The partoff tab width 33 may be different or the same as the actuator width 34. For example, the partoff tab width 33 may be smaller than the actuator width 34. For example, a narrower width may allow the partoff tab 30 to be more flexible (e.g., the force required to bend the partoff tab 30 may be reduced) than the actuator 32. For example, a larger actuator width 34 may help prevent the actuator 32 from buckling. The grain structure (e.g., ferrite, austenite, cementite, graphite or martensite) of the partoff tab 30, the actuator 32, the tubular structure 50, the cutter tube 10 or any combination thereof may be different from each other. For example, the partoff tab 30 may be annealed to reduce the stress when flexing. For example, the tubular structure 50 and the actuator 32 may be full hard to provide high strength and rigidity. The partoff tab 30 may have a partoff tab first end 40a and a partoff tab second end 40b. The partoff tab first end 40a and/or the partoff tab second end 40b may be secured—for example connected, attached, integrated, welded, adhered, glued, soldered, cut from the same original piece or any combination thereof—to the tubular system 20, the cutter tube 10, the tubular structure 50, the actuator 32 or any combination thereof. The cutter tube terminal distal end 12 of the cutter tube 10 may be sharpened. For example, the cutter tube terminal distal end 12 may be mechanically and/or chemically sharpened. The partoff tab 30 may have a tab edge 35a and/or 35b. The tab edge 35a and/or 35b may be sharpened. The tab edge 35a and/or 35b may have a sharp and/or chamfered edge. For example, the tab edge 35a and/or 35b may be cut with an off-axis laser to form a chamfered edge. The tab edge 35a and/or 35b may have a sharp edge and/or burr from a stamping operation. The tab edge 35a and/or 35b may be sharpened mechanically and/or chemically.

FIG. 2c illustrates that when the partoff mechanism 31 is in the coring configuration the partoff tab 30 may be flush and/or co-planar with the remainder of the cutter tube 10. For example, when in the coring configuration, the partoff tab 30 may extend into the inner diameter of the cutter tube 10 less than about 0.02in (0.5mm), or yet more narrowly less than about 0.01in (0.25mm) or yet more narrowly less than about 0.005in (0.13mm). A tissue sample may be cored by spinning the cutter tube 10 about the tubular longitudinal axis 8 while advancing the cutter tube 10 forward into a mass of tissue. When in the coring configuration, the partoff tab 30 may be in a longitudinally expanded configuration with an expanded longitudinal length 48a. A tab longitudinal axis 9 may pass longitudinally through the partoff tab 30.

The partoff tab 30 may be comprised of a partoff tab first length 49a and a partoff tab second length 49b. The tab longitudinal axis 9 may be parallel to the tubular longitudinal axis 8. The cutter tube 10 may contain multiple instances of the partoff mechanism 31, the partoff tab 30, the actuator 32 or any combination thereof. For example, the partoff mechanism 31 may be comprised of two or more instances of the partoff tab 30, which may be radially symmetric (i.e., symmetric about the tubular longitudinal axis 8) and/or may be located along the same tab longitudinal axis 9. For example, multiple instances of the partoff tab 30 may share the same tab longitudinal axis 9. The multiple instances of the partoff tab 30 can be actuated by the same actuator 32 or multiple instances of the actuator 32.

FIG. 2d illustrates that when the partoff mechanism 31 is in the partoff configuration the partoff tab 30 may extend into the inner diameter of the cutter tube 10. The partoff tab 30 may be in a longitudinally contracted position with a contracted longitudinal length 48b. The expanded longitudinal length 48a may be larger than the contracted longitudinal length 48b. The coring configuration may be used when the tool 5 is coring a sample and the partoff configuration may allow the tool 5 to partoff (i.e., part-off) a sample from a mass. The process of parting off may include severing a sample from the remainder of the mass. For example, the tool 5 may be advanced into a tissue mass in the coring configuration and then transition to the partoff configuration once a tissue sample is located within the cutter tube 10. Actuating the partoff mechanism 31 may partoff (i.e., separate and/or cut) the sample from the remainder of the mass. The partoff mechanism 31 may also longitudinally constrain a sample that has been severed and is located within the cutter tube 10; for example, the partoff tab 30 may obstruct a sample from entering and/or exiting through the cutter tube terminal distal end 12. The partoff tab 30 may be actuated by moving the actuator 32 relative to the cutter tube 10 and/or the cutter tube terminal distal end 12. For example, translating the actuator 32 in the direction of the cutter tube terminal distal end 12 may cause the partoff tab 30 to buckle and/or bend inwards. The partoff tab 30 may be actuated by translating the proximal end of the partoff tab 30 (e.g., the partoff tab second end 40b) relative to the cutter tube 10, the cutter tube terminal distal end 12, the tubular system 20 or any combination thereof. The cutter tube 10 may be spinning about the tubular longitudinal axis 8 while the partoff mechanism 31 is transitioning between the coring and partoff configurations. For example, if the cutter tube 10 is spinning while the partoff tab 30 is being bent inwards, then the tab edge 35a and/or 35b may partoff the tissue sample, thus severing the tissue sample completely from a tissue mass. The partoff mechanism 31 may be deployed to a known and/or controlled position. The partoff mechanism 31 may be used to shield the cutter tube terminal distal end 12 of the cutter tube 10. For example, the partoff tab 30 may be actuated as shown in FIG. 2d to prevent a tissue sample from exiting and/or entering through the cutter tube terminal distal end 12 of the cutter tube 10 when repositioning the tool 5. The actuator 32 may be comprised of a tube that is secured to the partoff tab 30; the actuator 32 may be located inside or outside of the cutter tube 10 and/or the tubular structure 50. The actuator 32 may be an extruded arc. The partoff tab 30 may contain multiple flex points 37a, 37b and/or 37c. A flex point can be an inflection point (i.e., the point of a change in curvature from concave to convex or from convex to concave) and/or a point of transition from a straight line to an arc or curve, or from an arc or curve to a straight line (referred to herein as a straight-curve transition point). For example, the flex points 37a and 37b, respectively, can be straight-curve transition points and the flex point 37c can be an inflection point. An inflection point may be located between the flex points 37a and 37c; an inflection point may be located between the flex points 37b and 37c. The flex points 37a, 37b and 37c may bend in different directions; for example, the flex points 37a and 37b may bend in a concave direction and the flex point 37c may bend in a convex direction.

FIG. 2e illustrates that when the partoff mechanism 31 is the partoff configuration, the partoff tab 30 may extend radially into the inner diameter of the cutter tube 10. The partoff tab 30 may extend approximately to the tubular longitudinal axis 8 of the cutter tube 10. The partoff tab 30 may extend past the tubular longitudinal axis 8, for example the partoff tab 30 may touch the opposite side of the cutter tube 10. The partoff tab 30 may extend a shorter distance, for example, it may not cross the tubular longitudinal axis 8. The partoff tab 30 may be comprised of the partoff tab first length 49a and a partoff tab second length 49b. The partoff tab first length 49a and the partoff tab second length 49b may meet at a vertex (e.g., the flex point 37c) and form a partoff angle 85. The partoff angle 85 may be approximately 180 degrees in a coring configuration and approximately 0 degrees in a partoff configuration. The partoff angle 85 may be larger than 180 degrees to position the partoff tab 30 outside of the cutter tube 10. The partoff angle 85 may be from about 160 degrees to about 180 degrees when coring. The partoff angle 85 may be from about 10 degrees to about 45 degrees when parting off The partoff tab 30 may be pre-flexed so that it is biased inwards when no force is applied; for example, the actuator 32 may apply a tensile force to the partoff tab 30 when in the coring configuration and a compressive force to the partoff tab 30 when in the partoff configuration. The partoff tab 30 may be pre-bent and/or conditioned to form a pre-determined profile when actuated. For example, the flex points 37a, 37b and/or 37c may have radii to reduce the stress at the flex points 37a, 37b and/or 37c; a larger radius may reduce the stress and/or strain on the material. A larger partoff angle 85 may reduce the stress at the flex points 37a, 37b and/or 37c. The partoff angle 85 may be controlled by the actuator 32. The actuator 32 may be used to adjust and/or control the partoff angle 85 and/or the radial position of the partoff tab 30. The stress and/or strain at flex points 37a, 37b and/or 37c may be designed to never exceed certain values, such as the ultimate tensile strength and/or yield strength of the material. Fatigue analysis may be performed on the partoff tab 30 to ensure that the component does not break, especially at flex points 37a, 37b and/or 37c; for example an S-N curve may be developed and/or referenced. If one of the flex points 37a, 37b or 37c break, then all components (including the partoff tab 30) may still be secured to the tool 5; this may result in a safer tool by reducing the risk of unintentional implants.

FIG. 2f illustrates that the tab edge 35a and/or 35b of the partoff tab 30 may have a tab angle 39. The tab angle 39 may be formed when cutting the partoff tab 30 (e.g., by stamping or using an off-axis laser cutter) or after cutting the partoff tab 30 (e.g., mechanical or chemical sharpening). The tab angle 39 may be from about 25 degrees to about 60 degrees, more narrowly from about 25 degrees to about 55 degrees. The tab angle 39 may allow the partoff tab 30 to cut through a mass easier, such as during partoff (e.g., if the partoff mechanism 31 is in the partoff configuration).

The internal diameter of the cutter tube 10 may be larger than about 0.04in (1.0mm), yet more narrowly larger than about 0.06in (1.5mm), yet more narrowly larger than about 0.08in (2.0mm), yet more narrowly larger than about 0.1in (2.5mm), yet more narrowly larger than about 0.12in (3.0mm), yet more narrowly larger than about 0.14in (3.5mm) or yet more narrowly larger than about 0.16in (4.0mm). The internal diameter of the cutter tube 10 may be less than about 0.16in (4.0mm), or yet more narrowly smaller than about 0.14in (3.5mm), or yet more narrowly smaller than about 0.12in (3.0mm), or yet more narrowly smaller than about 0.10in (2.5mm), or yet more narrowly smaller than about 0.08in (2.0mm), or yet more narrowly smaller than about 0.06in (1.5mm) or yet more narrowly smaller than about 0.04in (1.0mm).

The wall thickness of the cutter tube 10 may be larger than about 0.002in (0.05mm), or yet more narrowly larger than about 0.004in (0.10mm) or yet more narrowly larger than about 0.006in (0.15mm). The wall thickness of the cutter tube 10 may be smaller than about 0.006in (0.15mm), or yet more narrowly smaller than about 0.004in (0.10mm) or yet more narrowly smaller than about 0.002in (0.05mm). The wall thickness of the cutter tube 10 may vary. For example, the partoff tab 30 may have a different wall thickness than the actuator 32.

FIG. 3 illustrates that a straight wire 41 may be located inside of the cutter tube 10. The straight wire 41 may have a circular cross section and may conform to the internal diameter of the cutter tube 10. The cross-section of the straight wire 41 may be an arc; the straight wire 41 may be an extruded arc. For example, the actuator 32 may be constrained between the straight wire 41, the tube of the coaxial introducer 54 and the remainder of the cutter tube 10 and/or the tubular structure 50. The actuator 32 may be free to slide in the track created by the straight wire 41, the tube of the coaxial introducer 54 and the remainder of the cutter tube 10 and/or the tubular structure 50. The track may prevent the actuator 32 from buckling or bending (for example, when the partoff mechanism 31 is in the partoff configuration). The straight wire 41 may have a straight wire width 42. The straight wire width 42 may be larger than the actuator width 34. The straight wire 41 may be secured to the cutter tube 10. For example, the straight wire 41 may be welded, glued, soldered or any combination thereof to the cutter tube 10 and/or the tubular structure 50. The straight wire 41 may be a portion of the cutter tube 10 and/or the tubular structure 50 that can be bent internally. For example, the cutter tube 10 may be rolled from a flat piece of material into the shape of a tube, with the edges overlapping. For example, the cutter tube 10 may be stamped or formed to create a channel.

FIG. 4a and FIG. 4b illustrate that a spiral wire 43 may be located inside of the cutter tube 10 and/or the tubular structure 50. The spiral wire 43 may have a circular and/or rectangular cross section and may conform to the internal diameter of the cutter tube 10. The spiral wire 43 may be a flat wire bent into a helical shape. The spiral wire 43 may be cut from a piece of hypotube. For example, the actuator 32 may be constrained between the spiral wire 43, the tube of the coaxial introducer 54 and the remainder of the cutter tube 10 and/or the tubular structure 50. The actuator 32 may be free to slide in the track created by the spiral wire 43, the tube of the coaxial introducer 54 and the remainder of the cutter tube 10 and/or the tubular structure 50. The track may prevent the actuator 32 from buckling or bending (for example, when the partoff mechanism 31 is in the partoff configuration). The spiral wire 43 may be secured to the cutter tube 10 and/or the tubular structure 50. For example, the spiral wire 43 may be welded and/or glued to the cutter tube 10 and/or the tubular structure 50. The spiral wire 43 may be press fit and/or frictionally secured to the internal diameter of the cutter tube 10 and/or the tubular structure 50.

FIG. 5a and FIG. 5b illustrate that the actuator 32 may be constrained on the internal diameter and sides by the cutter tube 10 and/or the tubular structure 50. The actuator 32 may be cut from the cutter tube 10 and/or the tubular structure 50 at a tab cut 24a and 24b. The tab cut 24a and/or 24b may be thin and angled such that the actuator width 34 is larger than a cutter tube gap width 45. For example, the actuator 32 may be constrained by the cutter tube gap width 45, the tube of the coaxial introducer 54 and the remainder of the cutter tube 10 and/or tubular structure 50 on the sides. The tab cut 24a and/or 24b may be on-axis (i.e., radial). The tab cut 24a and/or 24b may be any angle. For example, the tab cut 24a and 24b may be parallel, perpendicular and/or co-linear with each other. The actuator 32 may be free to slide in the track created by the cutter tube gap width 45, the tube of the coaxial introducer 54 and the remainder of the cutter tube 10 and/or the tubular structure 50 on the sides. The track may prevent the actuator 32 from buckling or bending (for example, when the partoff mechanism 31 is in the partoff configuration).

FIG. 6a and FIG. 6b illustrate that a cantilevered tab 38 may be secured to and/or cut from the partoff tab 30. The cantilevered tab 38 may have a cantilevered tab width 47 and a cantilevered tab length 46. The partoff tab first and second lengths 49a and 49b may be secured to each other across the entire partoff tab width 33 or a portion of the partoff tab width 33. For example, the partoff tab first and second lengths 49a and 49b may be secured to each other with two ribs and a cutout in the center for the cantilevered tab 38. The cantilevered tab 38 may rest flush and/or co-planar with the remainder of the partoff tab 30 when in the coring configuration. When in the partoff configuration, the cantilevered tab 38 may extend past the partoff tab 30. For example, the cantilevered tab 38 may remain parallel to the partoff tab first length 49a and may extend further into the cutter tube 10 internal diameter than the flex point 37c. The cantilevered tab 38 may be cut from the partoff tab 30 and/or may be a separate element secured to the partoff tab 30. The cantilevered tab 38 may have a cantilevered tab edge 39a and/or 39b. The cantilevered tab edge 39a and/or 39b may be formed and/or sharpened similar to the partoff tab edge 35a and/or 35b. The cantilevered tab 38 may provide the same function as the partoff tab 30 (e.g., partoff a tissue sample and/or obstruct the cutter tube terminal distal end 12). The partoff tab 30 may contain multiple cantilevered tabs 38.

FIG. 7 illustrates a limiting tab 90 contacting a limiting port 91. The limiting tab 90 may be cut from the cutter tube 10, the tubular structure 50, the actuator 32 or any combination thereof. A limiting port 91 may be cut from the cutter tube 10, the tubular structure 50, the actuator 32 or any combination thereof. The limiting tab 90 may be bent to pass through and/or engage with the limiting port 91. The limiting tab 90 and the limiting port 91 may control the relative motion between the cutter tube 10, the tubular structure 50 the actuator 32 or any combination thereof. For example, the limiting tab 90 and the limiting port 91 may rotationally lock the cutter tube 10 and the actuator 32 in the clockwise and/or counter-clockwise directions. The limiting tab 90 and the limiting port 91 may limit the relative translation parallel with the tubular longitudinal axis 8 between the cutter tube 10, the tubular structure 50, the actuator 32 or any combination thereof; limiting the translation between the cutter tube 10, the tubular structure 50, the actuator 32 or any combination thereof may control the position of the partoff mechanism 31 (e.g., to limit the position of the partoff tab 30 and/or stresses induced in the partoff tab 30). The limiting tab 90 may be bent in a different orientation; for example, the limiting tab 90 may be oriented about 90 degrees (i.e., perpendicular) from how it is shown in FIG. 7 (this may provide more contact between the limiting tab 90 and the limiting port 91, which may reduce the friction and/or stresses).

FIG. 8a, FIG. 8b and FIG. 8c illustrate the partoff mechanism 31 with the partoff tab first and second lengths 49a and 49b and the cantilevered tab 38. The partoff tab first and second lengths 49a and 49b may be secured to each other at flex point 37c. The partoff tab first length 49a and the cantilevered tab 38 may be formed from the same element and may be secured to each other at the flex point 37c. For example, a first tab may be cut from the cutter tube 10 and/or the tubular structure 50 and secured to a secondar tab at the flex point 37c; the first tab will then be divided into a partoff tab first length 49a and a cantilevered tab 38. The cantilevered tab 38 may be another element that can be secured the partoff tab first length 49a and/or the partoff tab second length 49b. The cantilevered tab length 46 may be larger than about 0.04in (1.0mm), yet more narrowly larger than about 0.06in (1.5mm), yet more narrowly larger than about 0.08in (2.0mm), yet more narrowly larger than about 0.1in (2.5mm), yet more narrowly larger than about 0.12in (3.0mm), yet more narrowly larger than about 0.14in (3.5mm) or yet more narrowly larger than about 0.16in (4.0mm). The cantilevered tab length 46 may be less than about 0.16in (4.0mm), or yet more narrowly smaller than about 0.14in (3.5mm), or yet more narrowly smaller than about 0.12in (3.0mm), or yet more narrowly smaller than about 0.10in (2.5mm), or yet more narrowly smaller than about 0.08in (2.0mm), or yet more narrowly smaller than about 0.06in (1.5mm) or yet more narrowly smaller than about 0.04in (1.0mm). The partoff tab 30 may switch between a coring configuration (FIG. 8a) and a partoff configuration (FIG. 8b and FIG. 8c) by translating the partoff tab first length 49a relative to the partoff tab second length 49b. For example, pulling or pushing on the actuator 32 may adjust the partoff angle 85. The partoff tab second length 49b and/or the actuator 32 may be located on the inside or the outside of the cutter tube 10 and/or the tubular structure 50. The partoff tab second length 49b may extend back to the handle 6 and may be actuated by the partoff button 7. The flex point 37b may be where the partoff tab second length 49b and the actuator 32 are secured to each other. The flex point 37c may be located anywhere along the cutter tube 10, for example approximately 0.1 to 0.3 inches (i.e., 2.5mm to 7.5mm) proximal to the cutter tube terminal distal end 12. The partoff button 7 may be used to actuate and/or control the partoff mechanism 31. The partoff mechanism 31 may be actuated by controlling the temperature of at least one of the partoff tab first length 49a, the partoff tab second length 49b, the cutter tube 10 and the tubular structure 50. For example, the partoff tab first length 49a may have a different rate of thermal expansion than the partoff tab second length 49b, the cutter tube 10, the tubular structure 50 or any combination thereof. Increasing or decreasing the temperature of the partoff mechanism 31 may cause the partoff tab first length 49a to increase or decrease in length more than the partoff tab second length 49b (i.e., the ratio of expansion between the partoff tab first length 49a and the partoff tab second length 49b may be different), which may cause the partoff angle 85 to change the partoff tab first length 49a and the partoff tab second length 49b 0 may have the same coefficient of thermal expansion, but may be heated at different rates to result in different expansion. For example, the partoff tab first length 49a may be thinner than the partoff tab second length 49b (or vice-versa), and may heat up and expand faster than the partoff tab second length 49b (or vice-versa); for example, when heating the partoff mechanism 31, the partoff tab first length 49a and the partoff tab second length 49b may heat and/or cool at different rates, resulting in the partoff mechanism 31 going from a partoff configuration to a coring configuration and then back to a partoff configuration (as the temperatures transition from being equal to different to equal). The partoff tab first length 49a and the partoff tab second length 49b may cool differently, for example depending on their surface areas. The partoff tab first length 49a and/or the partoff tab second length 49b could expand and contract using a different technology. For example, the partoff tab first length 49a and/or the partoff tab second length 49b could be a piezoelectric or synthetic muscle actuator (e.g., electro-active polymers (EAPs)) which could be controlled with electricity and/or chemicals. FIG. 8c illustrates a cross-sectional view of the partoff mechanism 31 in an actuated configuration. When the partoff mechanism 31 is in the partoff configuration, the three flex points 37a, 37b and/or 37c may appear. The partoff angle 85 may be formed between the partoff tab first length 49a and the partoff tab second length 49b. The partoff angle 85 may be approximately 0 to 5 degrees when in the coring configuration and approximately 10-55 degrees when in the partoff configuration, yet more narrowly approximately 20-55 degrees.

FIG. 9a and FIG. 9b illustrate the partoff mechanism 31. The actuator 32 may be a tube. The actuator 32 may have a diameter that is smaller or larger than the tubular structure 50. The actuator 32 may be rotationally fixed to the tubular structure 50, for example using the limiting tab 90 and the limiting port 91. The actuator 32 may translate parallel to the tubular longitudinal axis 8 (i.e., axial translation) relative to the tubular structure 50. The actuator 32 and the tubular structure 50 may contain tabs to prevent relative rotation between the two elements while allowing axial translation. The partoff tab first end 40a may be secured to the tubular structure 50. The partoff tab second end 40b may be secured to the actuator 32. For example, the partoff tab first end 40a can be welded to the tubular structure 50 at a weld spot 51. The weld spot 51 may be a laser weld, a spot weld, a solder joint and/or an adhesive bond. When the tubular structure 50 translates relative the actuator 32, the partoff tab 30 may switch between the two configurations shown in FIG. 9a and FIG. 9b. The tool 5 may have a plane 92 parallel with the tubular longitudinal axis 8; for example, coincident with the tubular longitudinal axis 8. The distance from the plane 92 to the tubular longitudinal axis 8 can be fixed. As seen in FIGS. 9a & 9b at least two of the flex points 37 can remain in the plane 92 when the partoff tab 30 longitudinally contracts from the longitudinally expanded configuration shown in FIG. 9a to the longitudinally contracted configuration as shown in FIG. 9b. The angle of the plane 92 with respect to the tubular longitudinal axis 8 can be fixed. The plane 92 may pass through a point resting on the tubular longitudinal axis 8.

The cutter tube 10 may have a window 52. The window 52 may provide an exit for trapped tissue and/or mass. For example, when the partoff tab 30 switches from the configuration shown in FIG. 9b to the configuration shown in FIG. 9a, any material (e.g., tissue) trapped above the partoff tab 30 may escape through the window 52, allowing the partoff tab 30 to rest flush (e.g., co-planar) with the tubular structure 50 and/or the tubular system 20.

The partoff tab 30 may be secured to multiple elements, including the cutter tube 10, the tubular structure 50, the actuator 32 or any combination thereof. For example, if one of the flex points 37a, 37b or 37c breaks, the partoff tab 30 may still be secured to the tool 5. The partoff tab 30 may be able to generate high forces if it is secured to the tool 5 in multiple locations (e.g., flex points 37a and/or 37b). For example, the force applied to the actuator 32 may result in a radial force at the flex point 37c that may be approximately 40 to 60% higher than the force applied to the actuator 32.

The cutter tube 10 or any or all elements of the tool and/or other tools or apparatuses described herein can be made from or coated with, for example, single or multiple stainless steel alloys, steel, spring steel, nickel titanium alloys (e.g., Nitinol), cobalt-chrome alloys (e.g., ELGILOY® from Elgin Specialty Metals, Elgin, Ill.; CONICHROME® from Carpenter Metals Corp., Wyomissing, Pa.), nickel-cobalt alloys (e.g., MP35N® from Magellan Industrial Trading Company, Inc., Westport, Conn.), molybdenum alloys (e.g., molybdenum TZM alloy), tungsten-rhenium alloys, polymers such as polyethylene teraphathalate (PET), polyester (e.g., DACRON® from E. I. Du Pont de Nemours and Company, Wilmington, Del.), polypropylene, aromatic polyesters, such as liquid crystal polymers (e.g., Vectran, from Kuraray Co., Ltd., Tokyo, Japan), ultra high molecular weight polyethylene (i.e., extended chain, high-modulus or high-performance polyethylene) fiber and/or yarn (e.g., SPECTRA® Fiber and SPECTRA® Guard, from Honeywell International, Inc., Morris Township, N.J., or DYNEEMA® from Royal DSM N.V., Heerlen, the Netherlands), polytetrafluoroethylene (PTFE), Parylene poly(p-xylylene) polymers, Parylene N, Parylene C, Parylene D, expanded PTFE (ePTFE), polyether ketone (PEK), polyether ether ketone (PEEK), polycarbonate (PC), Acrylonitrile Butadiene Styrene (ABS), poly ether ketone ketone (PEKK) (also poly aryl ether ketone ketone), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), Nylon, Vinyl, polyurethane, thermoplastic, fluorinated ethylene propylene (FEP), absorbable or resorbable polymers such as polyglycolic acid (PGA), poly-L-glycolic acid (PLGA), polylactic acid (PLA), poly-L-lactic acid (PLLA), polycaprolactone (PCL), polyethyl acrylate (PEA), polydioxanone (PDS), and pseudo-polyamino tyrosine-based acids, extruded collagen, silicone, zinc, echogenic, radioactive, radiopaque materials, a biomaterial (e.g., cadaver tissue, collagen, allograft, autograft, xenograft, bone cement, morselized bone, osteogenic powder, beads of bone), a material with high strength (60 ksi) and biocompatibility, any of the other materials listed herein or combinations thereof. Examples of radiopaque materials are barium sulfate, zinc oxide, titanium, stainless steel, nickel-titanium alloys, tantalum and gold. The device can be made from substantially 100% PEEK, substantially 100% titanium or titanium alloy, or combinations thereof.

The cutter tube 10 may spin or rotate at a velocity relative to the handle 6 of greater than about 1,000 rpm, yet more narrowly larger than about 2,500 rpm, yet more narrowly larger than about 3,000 rpm, yet more narrowly larger than about 4,000 rpm, yet more narrowly larger than about 5,000 rpm, yet more narrowly larger than about 7,500 rpm, yet more narrowly larger than about 10,000 rpm. The cutter tube 10 may spin or rotate at a velocity relative to the handle 6 of less than about 10,000 rpm, yet more narrowly less than about 7,500 rpm, yet more narrowly less than about 5,000 rpm, yet more narrowly less than about 4,000 rpm, yet more narrowly less than about 3,000 rpm, yet more narrowly less than about 2,500 rpm, yet more narrowly less than about 1,000 rpm.

The internal diameter of the cutter tube 10 may be larger than about 0.5 mm (0.02 in), more narrowly larger than about 1 mm (0.04 in), yet more narrowly larger than about 1.5 mm (0.06 in), yet more narrowly larger than about 2 mm (0.08 in), yet more narrowly than about 2.5 mm (0.10 in), yet more narrowly larger than about 3 mm (0.12 in), yet more narrowly larger than about 3.5 mm (0.14 in), yet more narrowly larger than about 4 mm (0.18 in), yet more narrowly larger than about 4.5 mm (0.18 in), yet more narrowly larger than about 5 mm (0.20 in), yet more narrowly larger than about 6 mm (0.24 in), yet more narrowly larger than about 7 mm (0.28 in), or yet more narrowly larger than about 10 mm (0.39 in). The internal diameter of the cutter tube 10 may be less than about 10 mm (0.39 in), more narrowly less than about 7 mm (0.28 in), yet more narrowly less than about 6 mm (0.24 in), yet more narrowly less than about 5 mm (0.20 in), yet more narrowly less than about 4.5 mm (0.18 in), yet more narrowly less than about 4 mm (0.18 in), yet more narrowly less than about 3.5 mm (0.14 in), yet more narrowly less than about 3 mm (0.12 in), yet more narrowly less than about 2.5 mm (0.10 in), yet more narrowly less than about 2 mm (0.08 in), yet more narrowly less than about 1.5 mm (0.06 in), yet more narrowly less than about 1 mm (0.04 in), or yet more narrowly less than about 0.5 mm (0.02 in).

The wall thickness of the cutter tube 10 may be larger than about 0.05 mm (0.002 in), more narrowly larger than about 0.10 mm (0.004 in), yet more narrowly larger than about 0.15 mm (0.006 in), yet more narrowly larger than about 0.20 mm (0.008 in), yet more narrowly larger than about 0.30 mm (0.012 in), yet more narrowly larger than about 0.50 mm (0.020 in), yet more narrowly larger than about 0.70 mm (0.028 in), or yet more narrowly larger than about 1.00 mm (0.039 in). The wall thickness of the cutter tube 10 may be less than about 1.00 mm (0.039 in), yet more narrowly less than about 0.70 mm (0.028 in), yet more narrowly less than about 0.50 mm (0.020 in), yet more narrowly less than about 0.43 mm (0.017 in), yet more narrowly less than about 0.30 mm (0.012 in), yet more narrowly less than about 0.20 mm (0.008 in), yet more narrowly less than about 0.15 mm (0.006 in), yet more narrowly less than about 0.10 mm (0.004 in), or yet more narrowly less than about 0.05 mm (0.002 in).

The straight wire 41 and/or the spiral wire 43 may increase torsional traction (e.g., deliver rotational force) between the tissue sample and the cutter tube 10. The straight wire 41 and/or the spiral wire 43 may not significantly impact traction (e.g., delivering no longitudinal force and providing minimal or no counter force in the longitudinal direction) in the longitudinal direction between the tissue sample and the straight wire 41 and/or the spiral wire 43. The straight wire 41 and/or the spiral wire 43 may be examples of surface features.

The coaxial introducer 54 and/or the actuator 32 may be actuators. Multiple tissue samples can be collected and/or obtained and/or parted-off without removing the tool from the mass of tissue (i.e., tissue mass).

U.S. patent application Ser. Nos. 13/653,395, filed Oct. 16, 2012; 13/452,863, filed Apr. 21, 2012, International Application No. PCT/US 2011/061089, filed Nov. 16, 2011, and U.S. Provisional Application No. 61/415,850, filed Nov. 21, 2010, are all incorporated by reference herein in their entireties.

It is apparent to one skilled in the art that various changes and modifications can be made to this disclosure, and equivalents employed, or combinations of any of the disclosed elements, characteristics, features, devices, tools, steps, or methods without departing from the spirit and scope of the invention. Any of the disclosed elements, characteristics, features, devices, tools, steps, or methods can be present as a singular or as a plurality regardless of whether the elements, characteristics, features, devices, steps, or methods are explicitly disclosed herein as being singular or as a plurality. Elements shown with any variation are exemplary for the specific variation and can be used on other variation within this disclosure.

What is claimed is:

1. A tool for acquiring a tissue comprising:
   an inner tube;
   an outer tube located concentrically outside the inner tube, wherein the outer tube comprises an open distal end;
   a partoff tab comprising a rectangular shaped projection that projects from a distal end of the inner tube, wherein a first end of the partoff tab is coupled to the distal end of the inner tube and the second end of the partoff tab is coupled to the outer tube; and
   a handle interoperative with the inner tube and the outer tube,
   wherein the inner tube and the outer tube are configured to rotate with respect to the handle while rotationally fixed with respect to each other.

2. The tool of claim 1, wherein the partoff tab has a longitudinally expanded configuration and a longitudinally contracted configuration.

3. The tool of claim 2, wherein the partoff tab has a plurality of flex points, and at least two of the plurality of flex points remain in a plane when the partoff tab longitudinally contracts from the longitudinally expanded configuration to the longitudinally contracted configuration.

4. The tool of claim 2, wherein a first length of the partoff tab along a tubular longitudinal axis in the longitudinally expanded configuration is longer than a second length of the partoff tab along the tubular longitudinal axis in the longitudinally contracted configuration.

5. The tool of claim 1, wherein the partoff tab is configured to be actuated by moving an actuator relative to the inner tube.

6. The tool of claim 1, wherein the inner tube is configured to rotate about a tubular longitudinal axis while the partoff tab transitions between a coring configuration and a partoff configuration.

7. The tool of claim 1, wherein the partoff tab is configured to cut the tissue and contain the tissue.

8. The tool of claim 1, wherein the handle comprises a battery.

9. A tool for acquiring a tissue comprising:
   an inner tube comprising a single partoff tab with chamfered lateral edges, wherein the single partoff tab is transitionable between a coring configuration and a partoff configuration, and wherein the partoff tab in the partoff configuration extends radially into the inner tube beyond a central longitudinal axis of the inner tube;
   an outer tube located concentrically outside the inner tube, wherein the outer tube comprises an open distal end;
   a handle interoperative with the inner tube and the outer tube; and
   an introducer located concentrically outside the inner tube and the outer tube and configured to be rotationally and longitudinally fixed with respect to the handle, wherein:
   the inner tube and the outer tube are configured to rotate with respect to the handle while rotationally fixed with respect to each other.

10. The tool of claim 9, wherein the inner tube is configured to rotate about a tubular longitudinal axis while the partoff tab transitions between the coring configuration and the partoff configuration.

11. The tool of claim 9, wherein the handle comprises a battery.

12. The tool of claim 1, wherein the partoff tab comprises chamfered lateral edges.

13. The tool of claim 1, wherein partoff tab is a single partoff tab that projects from the distal end of the inner tube.

* * * * *